United States Patent
Ruppert et al.

(10) Patent No.: US 7,601,767 B2
(45) Date of Patent: *Oct. 13, 2009

(54) COMPOSITE MATERIALS HAVING A LOW SHRINKAGE FORCE

(75) Inventors: Klaus Ruppert, Maintal (DE); Andreas Grundler, Wuppertal (DE); Kurt Reischl, Merenberg (DE); Michael Eck, Schmitten (DE); Alfred Hohmann, Schmitten (DE); Christine Diefenbach, Dornburg (DE)

(73) Assignee: Heraeus Kutzer GmbH, Hanau (DE)

( * ) Notice: Subject to any disclaimer, the term of this patent is extended or adjusted under 35 U.S.C. 154(b) by 383 days.

This patent is subject to a terminal disclaimer.

(21) Appl. No.: 11/408,534

(22) Filed: Apr. 21, 2006

(65) Prior Publication Data

US 2006/0252845 A1 Nov. 9, 2006

(30) Foreign Application Priority Data

May 4, 2005 (DE) ........................ 10 2005 021 332

(51) Int. Cl.
- A61K 6/083 (2006.01)
- A61K 6/09 (2006.01)
- C08K 3/40 (2006.01)
- A61C 5/00 (2006.01)

(52) U.S. Cl. ........................ 523/116; 523/117; 524/493; 524/494; 433/228.1

(58) Field of Classification Search ................ 523/116, 523/117; 524/493, 494
See application file for complete search history.

(56) References Cited

U.S. PATENT DOCUMENTS

| | | | |
|---|---|---|---|
| 4,629,746 A | 12/1986 | Michl et al. | |
| 4,649,165 A | 3/1987 | Kuhlmann | |
| 5,228,907 A | 7/1993 | Eppinger et al. | |
| 5,750,590 A | 5/1998 | Schaefer et al. | |
| 5,936,006 A | 8/1999 | Rheinberger et al. | |
| 6,063,831 A | 5/2000 | Kubo et al. | |
| 6,353,039 B1* | 3/2002 | Rheinberger et al. | 523/109 |
| 6,362,251 B1 | 3/2002 | Alkemper et al. | |
| 6,387,981 B1 | 5/2002 | Zhang et al. | |
| 6,482,004 B1 | 11/2002 | Senn et al. | |
| 6,572,693 B1 | 6/2003 | Wu et al. | |
| 6,593,395 B2 | 7/2003 | Angeletakis et al. | |
| 6,620,864 B2 | 9/2003 | Schmid | |
| 6,706,356 B2* | 3/2004 | Lee | 428/40.1 |
| 6,709,271 B2 | 3/2004 | Yin et al. | |
| 6,783,810 B2 | 8/2004 | Jin et al. | |
| 6,855,197 B2 | 2/2005 | Su et al. | |
| 2004/0253383 A1* | 12/2004 | Belik et al. | 427/384 |
| 2005/0065227 A1 | 3/2005 | Condon | |
| 2006/0058414 A1* | 3/2006 | Arthur et al. | 523/116 |

FOREIGN PATENT DOCUMENTS

| | | |
|---|---|---|
| DE | 34 03 040 C2 | 8/1985 |
| DE | 35 02 594 | 7/1986 |
| DE | 196 17 931 | 11/1997 |
| DE | 198 51 038 | 7/1999 |
| DE | 199 05 093 | 8/2000 |
| DE | 199 13 890 | 9/2000 |
| EP | 0486775 | 8/1991 |
| EP | 10 29 880 | 8/2000 |
| EP | 1 387 658 | 2/2004 |
| WO | WO 00/21488 | 4/2000 |
| WO | WO 01/30304 | 5/2001 |
| WO | WO 01/30305 | 5/2001 |
| WO | 10 2004 017 124 | 11/2005 |

OTHER PUBLICATIONS

Claus-Peter Ernst, Nicole Brand, Ulrike Frommator, Gerd Rippin, Brita Willershausen. Reduction of polymerization shrinkage stress and marginal microleakage using soft-start polymerization. Journal of Esthetic and Restorative Dentistry (2003); 15: 93-103. BC Decker Inc.

S.H. Kim, D.C. Watts. Polymerization shrinkage-strain kinetics of temporary crown and bridge materials. Dental Materials (2004); 20: 88-95. Elsevier Ltd.

Claus-Peter Ernst, Gerrit R. Meyer, Kerstin Klöcker, Brita Willershausen, Determintation of polymerization shrinkage stress by means of a photoelastic investigation. Dental Materials (2004); 20; 313-321. Elsevier Ltd.

* cited by examiner

*Primary Examiner*—Tae H Yoon
(74) *Attorney, Agent, or Firm*—Norris, McLaughlin & Marcus, P.A.

(57) ABSTRACT

For composite materials having a total filler content of 80 to 95% by weight, containing A) 0.5 to 10% by weight of non-agglomerated nanofillers having particle sizes of 1 to 50 nm in the filler component, B) at least 60% by weight of a filler mixture of 50 to 90% coarse-particle and 10 to 50% fine-particle dental glass in the filler component, having a size ratio, relative to the average particle size ($d_{50}$ value), of coarse to fine particles of >1:4 to 1:30, C) as monomer component, a monomer mixture of
  i. 60 to 80% bis-GMA or TCD-di-HEMA or TCD-di-HEA,
  ii. 10 to 18% UDMA,
  iii. Residual TEDMA and/or multifunctional crosslinkers, D) up to 1% photoinitiator(s); and E) optionally, at least one additional dental glass in the filler component having a different particle size than the coarse- and fine-particle dental glass, the polymerization shrinkage may be reduced to <1.6% by volume (measured according to the bonded disk method; Dental Materials (2004) 20, 88-95), and the shrinkage force (measured according to the photoelastic method; Dental Materials (2004) 20, 313-321) may be reduced to <3.5 MPa (measured 24 hours after polymerization).

14 Claims, No Drawings

COMPOSITE MATERIALS HAVING A LOW SHRINKAGE FORCE

The invention relates to composite materials having a low shrinkage force.

BACKGROUND OF THE INVENTION

Light-curing substances based on acrylate/methacrylate undergo volume shrinkage during radical polymerization due to the reduced molecular distance resulting from the polymerization and the associated increase in density. This shrinkage may be significantly reduced by adding inorganic fillers such as dental glass or pyrogenic silicic acids, since a reduced monomer proportion per unit volume is obtained, and the fillers do not shrink during the polymerization.

Volume shrinkage has great clinical importance for dental applications, since tensile forces are transmitted to the cavity wall as the result of material shrinkage. When a maximum force is exceeded, in extreme cases this shrinkage force may lead to detachment from the cavity wall. Bacteria may infiltrate the peripheral gap thus created, causing secondary dental caries.

An observation of the progression of the shrinkage force over time results in the following typical findings:

Directly after the polymerization, the volume shrinkage results in an initial value for the shrinkage force which then increases to a maximum value within about 24 hours due to post-polymerization. Absorption of water (in the laboratory, from storage in water, or in the mouth, from saliva) after several days to weeks causes a slight volume expansion of the composite, and the stress forces may relax once again and return to a lower level.

As a result, the decisive influencing variable is the maximum shrinkage stress value after approximately 24 hours, since this parameter represents the maximum force load of the combined composite/adhesive/tooth system.

There have been many attempts to provide low-shrinkage dental materials: DE 199 05 093 A1 proposes the use of bicyclic monomers which cure via ring-opening metathesis polymerization (ROMP). According to DE 198 51 038 A1, the shrinkage is controlled by adding acryloylmorpholine, cumarone resin, vinyl stearate, polyvinyl acetate, or alcohol surfactants before polymerization. According to U.S. Pat. No. 5,750,590, cationically polymerizable "oxetanes" (trimethylene oxides) have low shrinkage and therefore are also suitable for reduced-shrinkage dental materials. U.S. Pat. No. 6,855,197 B2 describes reduced-shrinkage filler materials based on epoxy resin, containing nanoscale inorganic oxides as fillers. According to U.S. Pat. No. 6,709,271 B2, use of a filler mixture composed of spherical fillers having a particle size of 200-500 nm and submicron fillers having a particle size of 20-80 nm results in shrinkage of up to 1.8% following polymerization.

The present patent application relates primarily to the shrinkage force and the reduction of same. In addition to the material properties described above by way of example, the shrinkage force also influences processing parameters:

Luminous Power

A light curing device having a pulse mode operation for eliminating shrinkage force problems is proposed in DE 199 13 890 A1.

Polymerization kinetics: For identical composite materials, lower shrinkage forces may be achieved by an initially slower polymerization at lower luminous power, followed by an increase in the luminous power to the maximum value (soft-start polymerization). As a result of the lower luminous power at the beginning, the composite material remains flowable for a longer period, and therefore is better able to compensate for and reduce stress (J. Esthet. Restor. Dent. (2003) 15, 93-104). In US 20050065227 A1 it is presumed that in the use of multifunctional photoinitiators the early stages of shrinkage occur as long as the material is still elastic, ultimately resulting in lower shrinkage stress.

Geometry of the restorative: Shrinkage forces may be minimized by use of an incremental technique in building the restorative (U.S. Pat. No. 6,783,810 B2). However, the more layers that must be individually cured, the more time required by the dentist to provide treatment.

SUMMARY OF THE INVENTION

The object of the present invention is to provide a composite material for dental applications, which on the basis of its material properties significantly reduces the risk of detachment of the restorative from the cavity wall by reducing the maximum force of the shrinkage stress.

According to the invention, this object is achieved by the following measures:

By use of non-agglomerated nanofillers (e.g., $SiO_2$, $ZrO_2$, $TiO_2$, $Al_2O_3$) having particle sizes<50 nm as filler component, a significantly higher total filler content (>80 to 95% by weight) may be achieved compared to conventional products such as aerosils, e.g., thereby reducing the proportion of the shrinkable monomer matrix.

By use of a filler mixture of coarse- and fine-particle dental glass having a size ratio of >1:4 to 1:30, preferably >1:4 to 1:20, particularly preferably approximately 1:5 to 1:10, better packing of the filler particles, and therefore a higher filler proportion, may be achieved. The higher filler proportion results in a lower proportion of the shrinkable monomer matrix (see above). The proportion of fine-particle dental glass must not exceed a maximum of 40% of the filler mixture.

In dental applications, a monomer mixture composed of bis-GMA and TEDMA is typically used. Bis-GMA is used in a proportion of 60-80%, and TEDMA is used in a proportion of 20-40%. The bis-GMA represents the low-shrinkage component, which however due to its very high viscosity must be combined with a high-shrinkage diluent (TEDMA). Substitution of essentially all the high-shrinkage diluent TEDMA by UDMA (urethane dimethacrylate), which is much less reactive, reduces the volume shrinkage. Surprisingly, the solubility does not increase, despite the lower reactivity of the UDMA and the reduced incorporation into the polymer network assumed to occur as a result.

The dental materials with reduced shrinkage and shrinkage force may likewise be produced by the use of tricyclodecane derivatives such as SR 833S (Sartomer), Plex 6759-O (Röhm), CD-di-HEMA (bis(methacryloyloxymethyl)tricyclo[$5.2.10^{2,6}$]decane), or TCD-di-HEA (bis(acryloyloxymethyl)tricyclo[$5.2.10^{2,6}$]decane)-2-propenoic acid, (octahydro-4,7-methane-1H-indene-5-diyl) bis(methyleneiminocarbonyloxy-2,1-ethanediyl)ester, or the analogous HEMA derivative (TCD-di-HEMA) as main component(s) instead of bis-GMA.

In addition to these measures, the content of photoinitiators may optionally be reduced, e.g., to 0.3 or 0.1% by weight, thereby further reducing the proportion of unreacted monomers and thus the polymerization shrinkage as well.

DETAILED DESCRIPTION

Consequently, the invention relates to composite materials having a shrinkage force of <4.0, preferably <3.75, particularly preferably <3.5 MPa, measured 24 hours after the polymerization according to the photoelastic method set forth in Dental Materials 20, 313-321 (2004), in particular composite materials having a total filler content of 80 to 95% by weight, containing A) 0.5 to 10% by weight of non-agglomerated nanofillers having particle sizes of 1 to 50 nm in the filler component;
B) at least 60% by weight of a filler mixture of 50 to 90% coarse-particle and 10 to 50% fine-particle dental glass in the filler component, having a size ratio, relative to the average particle size ($d_{50}$ value), of coarse to fine particles of >1:4 to 1:30;
C) as monomer component, a monomer mixture of
   i. 60 to 80% bis-GMA or TCD-di-HEMA or TCD-di-HEA
   ii. 10 to 18% UDMA
   iii. Residual TEDMA and/or multifunctional crosslinkers;
D) up to 1% initiator(s); and
E) optionally, at least one additional dental glass in the filler component having a different particle size than the coarse- and fine-particle dental glass.

Non-agglomerated nanofillers are known as such, and are described, e.g., in WO 0130305 A1 or in the example of $SiO_2$ in DE 196 17 931 A1. According to the invention, these materials are preferably included in the group composed of $SiO_2$, $ZrO_2$, $TiO_2$, $Al_2O_3$, and mixtures of at least two of these substances.

The non-agglomerated nanofillers may be dispersed in organic solvents, as described in DE 196 17 931 A1, or may also be dispersed in water or solvent mixtures containing water.

Barium glass powder and/or strontium glass powder are particularly suitable as dental glass. The average particle size of the coarse-particle dental glass is preferably 5 to 10 µm, in particular approximately 7 µm, and the average particle size of the fine-particle dental glass is preferably 0.5 to 2 µm, in particular 1 µm. Additional dental glass optionally present has an average particle size of 2-5 or 10-50 µm.

Thus, the filler component may contain dental glass having a total of three or more particle sizes. The filler component may also contain additional, conventional fillers customarily used in dentistry, such as quartz, ceramic glass, or mixtures thereof. The composites may also contain fillers for achieving an increased X-ray opacity. The average particle size of the X-ray-opaque filler is preferably 100 to 300 nm, in particular 180 to 300 nm. The fluorides of the rare earth metals, i.e., the trifluorides of elements 57 through 71, as described in DE 35 02 594 A1 are suitable as X-ray-opaque fillers. A particularly preferred filler is ytterbium fluoride, in particular ytterbium trifluoride, having an average particle size of approximately 300 nm. The quantity of X-ray-opaque filler is preferably 10 to 50% by weight, particularly preferably 20 to 30% by weight, relative to the total filler content.

Precipitated mixed oxides such as $ZrO_2/SiO_2$, e.g., may also be used as fillers. Preferred are mixed oxides having a particle size of 200 to 300 nm, in particular approximately 200 nm. The mixed oxide particles are preferably spherical and have a uniform size. The mixed oxides preferably have an index of refraction of 1.52 to 1.55. Precipitated mixed oxides preferably are used in quantities of 25 to 75% by weight, in particular, 40 to 75% by weight.

The fillers are preferably silanized for improving the adhesion between the filler and the organic matrix. Particularly suitable as a bonding agent is alpha-methacryloxypropyltrimethoxysilane. The quantity of bonding agent used depends on the nature and the BET surface of the filler.

Besides TEDMA and UDMA, the following multifunctional crosslinkers may also be considered: diethylene glycol di(meth)acrylate, decanedioldi(meth)acrylate, trimethylolpropanetri(meth)acrylate, and pentaerythrite tetra(meth)acrylate, as well as butanedioldi(meth)acrylate, 1,10-decanedioldi(meth)acrylate, and 1,12-dodecanedioldi(meth)acrylate.

For initiating the polymerization, the composites contain a polymerization initiator, e.g., an initiator for the radical polymerization. Depending on the type of initiator used, the mixtures can be polymerized cold, by use of light, or hot.

As initiators for hot polymerization, the known peroxides such as dibenzoyl peroxide, dilauroyl peroxide, tert-butyl peroctoate, or tert-butyl perbenzoate may be used, but alpha, alpha'-azo-bis(isobutyroethyl ester), benzpinacol, and 2,2'-dimethylbenzpinacol are also suitable.

As photoinitiators, benzoin alkyl ethers or esters, benzil monoketals, acyl phosphine oxides, or aliphatic and aromatic 1,2-diketo compounds, such as 2,2-diethoxyacetophenone, 9,10-phenanthrenequinone, diacetyl, furil, anisil, 4,4'-dichlorobenzil, and 4,4'-dialkoxybenzil or camphorquinone may be considered. Photoinitiators are preferably used together with a reducing agent. Examples of reducing agents include amines such as aliphatic or aromatic tertiary amines, for example N,N-dimethyl-p-toluidine or triethanolamine, cyanoethylmethylaniline, triethylamine, N,N-dimethylaniline, N-methyldiphenylamine, N,N-dimethyl-sym-xylidine, N,N-3,5-tetramethylaniline, and 4-dimethylaminobenzoic acid ethyl ester, or organic phosphites. Examples of common photoinitiator systems include camphorquinone plus ethyl-4-(N, N-dimethylamino)benzoate, 2-(ethylhexyl)-4-(N,N-dimethylamino)benzoate, or N,N-dimethylaminoethylmethacrylate.

As initiator for the UV light-initiated polymerization, 2,4, 6-trimethylbenzoyldiphenylphosphine oxide is particularly suited. UV photoinitiators may be used alone, or in combination with an initiator for visible light, an initiator for cold curing, and/or an initiator for hot curing.

As initiators for cold polymerization, radical-donating systems, for example benzoyl or lauroyl peroxide together with amines such as N,N-dimethyl-sym-xylidine or N,N-dimethyl-p-toluidine, are used.

Dual-curing systems may also be used, such as photoinitiators with amines and peroxides.

The initiators are preferably used in quantities of 0.01 to 1% by weight, relative to the total mass of the mixture.

In cold polymerization, it may be suitable for the composite material to be present divided into two components which are provided for curing by admixture. The material may also be provided so that is cured both by light and by admixture of two components.

The composite materials according to the invention preferably have a polymerization shrinkage of <2.0% by volume, in particular <1.8% by volume, very particularly preferably <1.6% by volume (measured according to the bonded disk method; Dental Materials (2004) 20, 88-95).

As dental materials, composite materials according to the invention have a shrinkage force (measured according to the photoelastic method; Dental Materials (2004) 20, 313-321) of <4.0, preferably <3.75, particularly preferably <3.5 MPa (measured 24 hours after polymerization).

We claim:
1. Composite material having a total filler content of 60.5 to 95% by weight, containing

A) 0.5 to 10% by weight of non-agglomerated nanofillers having particle sizes of 1 to 50 nm;
B) at least 60% by weight of a further filler mixture of 50 to 90% coarse-particle and 10 to 50% fine-particle dental glass, having a size ratio, relative to the average particle size ($d_{50}$ value), of coarse to fine particles of >1:4 to 1:30;
C) 5-39.5% by weight of a monomer component, comprising a mixture of
  i. 60 to 80% by weight bis-GMA (bisphenol A glycidyl methacrylate) or TCD-di-HEMA ((bis(methacryloyloxymethyl)tricyclo[$5.2.10^{2,6}$]-decane) or TCD-di-HEA (bis(acryloyloxymethyl)-tricyclo[$5.2.1.0^{2,6}$]decane),
  ii. 10 to 18% by weight UDMA (urethane dimethacrylate),
  iii. Residual TEDMA (triethylene glycol dimethacrylate) and/or multifunctional crosslinkers;
D) up to 1% by weight initiator(s).

2. Composite material according to claim 1, containing D) in a proportion up to 1% by weight initiator(s) for curing with light.

3. Composite material according to claim 1, containing
D) initiators for cold or hot curing and also photoinitiators, for curing by admixture in combination with light curing.

4. Composite material according to claim 1, wherein the size ratio of coarse to fine particles is >1:4 to 1:20.

5. Composite material according to claim 1, wherein the size ratio of coarse to fine particles is >1:5 to 1:10.

6. Composite material according to claim 1, further comprising
E) at least one additional dental glass in the filler component having a different particle size than the coarse- and fine-particle dental glass.

7. Composite material according to claim 1, wherein component D is present in a proportion up to 0.3% by weight.

8. Composite material according to claim 1, wherein component D is present in a proportion up to 0.1% by weight.

9. Composite material according to claim 1, wherein the average particle size of the coarse-particle dental glass is 7 μm, and the average particle size of the fine-particle dental glass is 1 μm.

10. Composite material according to claim 1, wherein the nanofillers are selected from the group consisting of $SiO_2$, $ZrO_2$, $TiO_2$, $Al_2O_3$, and mixtures of at least two of these substances.

11. Composite material according to claim 1, having a polymerization shrinkage of <2.0% by volume, measured according to the bonded disk method (Dental Materials 20, 88-95 (2004)).

12. Composite material according to claim 11, having a polymerization shrinkage of <1.8% by volume.

13. Composite material according to claim 12, having a polymerization shrinkage of <1.6% by volume.

14. A dental material comprising the composite material of claim 1.

* * * * *